United States Patent [19]
Cohen et al.

[11] 3,980,722
[45]*Sept. 14, 1976

[54] PRODUCTION OF BROMOSTYRENE, DIBROMOSTYRENE AND ALKYL BROMIDES

[75] Inventors: Ella Cohen, Ramat Hasharon; Stephen Daren, Rehovot; Moshe Levy, Rehovot; David Vofsi, Rehovot, all of Israel

[73] Assignee: Yeda Research & Development Co. Ltd., Rehovot, Israel

[ * ] Notice: The portion of the term of this patent subsequent to Feb. 18, 1992, has been disclaimed.

[22] Filed: July 3, 1973

[21] Appl. No.: 376,171

[30] Foreign Application Priority Data
July 4, 1972    Israel...................................... 39817

[52] U.S. Cl............................... 260/650 R; 260/657
[51] Int. Cl.²......................................... C07C 25/28

[58] Field of Search......................... 260/650 R, 657

[56] References Cited
UNITED STATES PATENTS
3,867,468    2/1975    Vofsi et al...................... 260/650 R

*Primary Examiner*—D. Horwitz
*Attorney, Agent, or Firm*—Hubbell, Cohen, Stiefel & Gross

[57] ABSTRACT

A process for the simultaneous production of bromostyrene or dibromostyrene and of an alkyl bromide, which comprises reacting bromoethyl bromobenzene or bromoethyl dibromobenzene with an alkanol at an elevated temperature. When only these reactants are reacted, the temperature is between 400°C and 550°C; when the reaction is effected in the presence of a source of free radicals, the temperature used can be lower, and temperatures of about 300°C are adequate.

6 Claims, No Drawings

PRODUCTION OF BROMOSTYRENE, DIBROMOSTYRENE AND ALKYL BROMIDES

BACKGROUND OF THE INVENTION:

In U.S. Patent No. 3,737,469 issued June 5, 1973, there is described and claimed a process for the simultaneous production of bromostyrene and methyl bromide which comprises reacting α-bromoethyl bromobenzene or p-bromoethyl bromobenzene ( "the substrate " ) and methanol in a medium of certain molten inorganic salts.

A known process for the production of bromostyrene comprises effecting a dehydration of the respective bromophenyl methyl carbinol, or the respective bromophenyl ethyl alcohol. Another known process is the dehydrobromination of either of the respective α- or p-haloethyl mono-bromobenzene isomers.

This latter method is exemplified in British Patent No. 986,634. The dehydrobromination of bromoethyl halobenzenes is effected by passing a mixture of the reactants together with an excess of steam over granular calcium sulfate catalyst. The use of calcium sulfate as catalyst is also mentioned in U.S. Pat. No. 2,485,524 in vapor-phase dehydrohalogenations of substituted halo-benzenes. Other catalysts mentioned in the literature for dehydrohalogenations are calcium chloride, calcium oxide, calcium phosphate and various aluminas.

When applied to bromoethyl bromobenzene, all of these catalysts exhibit the serious drawback of causing the formation and deposition on the catalyst of tarry substances, most probably comprising a polymer formed from the monomeric bromostyrene which is the primary product of the catalytic dehydrohalogenation. The formation of the polymer cannot be avoided, even when a large excess of an inert diluent, such as steam or nitrogen, is fed together with the substrate into the reaction zone. The deposition of the polymer on the catalyst reduces rapidly its activity and thus frequent catalyst regenerations are required. If the catalyst is discarded after relatively brief runs, the recharging with fresh catalyst is a comparatively expensive operation.

To eliminate the deposition of the tarry byproducts on the fixed bed of the catalyst, a process is described in French patent No. 1,576,909, wherein the active catalyst as well as the reaction medium comprises certain mixtures of molten salts, and in particular mixtures containing bivalent metal chlorides, such as copper chloride, in combination with other salts which decrease the melting point of the salt mixture.

While according to the above disclosure it is possible to obtain, for example, high yields of vinyl chloride by the elimination of hydrogen chloride from ethylene dichloride, the said process produces only poor yields of monomers in the case of heavy, relatively non-volatile substrates. In particular, when the substrates according to the present invention are used, the conversion to the respective products is far from complete.

In U.S. Pat. No. 3,737,469 a process was described whereby molten salts were used very effectively as reaction medium for the production of bromostyrene by passing through this medium the said substrate together with a reactive diluent, such as an aliphatic alcohol, and in particular methyl alcohol. The term "reactive diluent" designates a suitable substance which act is as an acceptor — or scavanger — for the hydrogen halide which is eliminated from the substrate during the reaction.

It is believed that the fast reaction of the "reactive diluent" with the eliminated hydrogen halide has a pronounced beneficial effect on the yield of the desired product for two reasons. It is known that elimination of hydrogen halide from the substrate is a reversible reaction. It it is carried out in the presence of an acceptor for the hydrogen halide that is being eliminated — the equilibrium is shifted in the direction of the product, and the process can thereby be carried out at temperature that are substantially lower than in the absence of the acceptor. This has the effect of increasing the selectivity of the reaction with respect to the desired product.

The enhanced selectivity of the reaction, which is achieved in the presence of the "reactive diluent" is believed to be a consequence also of the prompt removal of the hydrogen halide from the system, since this is known to catalyze the polymerization of vinylic monomers to produce oligomeric materials, which are highly undesirable.

Another advantage in use of "reactive diluents" is the rational utilization of the bromine.

By reacting the hydrogen bromide, which is eliminated from the bromoethyl — bromobenzene, with the "reactive-diluent," useful and highly valued by-products are directly obtained instead of hydrobromic acid, which has a lower "bromine value."

As "reactive-diluents" may be employed lower aliphatic alcohols and the by-products are the respective alkyl halides. When methanol is used in conjunction with the substrate, methyl bromide is obtained in quantitative yield. When ethyl alcohol is used the resulting by-product is ethyl bromide. These are widely used as soil sterilizers and fumigants, as well as fire extinguishing agents.

While results according to U.S. Pat. No. 3,737,469 are generally satisfactory — the said process has certain insufficiencies such as for instance the need for special materials of construction to be used for the reactors containing highly corrosive molten salts. Another drawback of said process is in the high ratio of reactor-space to product produced in unit time (low space-time yields).

A further drawback is the formation of small quantities of saturated products such as ethyl bromobenzenes. These products have boiling points very close to that of bromostyrene, and it is therefore very difficult to separate them by fractional distillation. Furthermore, these products are not polymerisable and even act as chain transfer agents, thus decreasing the molecular weight of the produced polymers. According to the present invention a high purity monomer is obtained albeit the conversions are lower than in the aforementioned patent.

The present invention relates to a process for the production of either bromostyrene or dibromostyrene, together with an alkyl bromide, by reacting bromoethyl bromobenzene or bromoethyl-dibromobenzene, respectively, with a lower alkanol at an elevated temperature in the gaseous phase. When only these reactants are used, this is a pyrolysis reaction, and the reaction is advantageously effected at a temperature in the range of about 400°C and 550°C. A further improvement of the process according to the present invention comprises effecting it in the presence of catalytic quantities of peroxides or of other sources of free radicals. By the use of such additives, there may be used a much lower temperature of reaction, and the reaction proceeds at a satisfactory rate even at temperatures as low as 280°C.

Bromostyrene is a reactive monomer which can be polymerized to a hard, transparent plastic which has many uses. It can be copolymerized with other monomers to result in copolymers which are fire retardant and self-extinguishing. It is of particular interest as a reactive component in unsaturated polyester compositions, to result in self-extinguishing transparent plastic compositions, that do not become discoloured upon prolonged exposure to weather conditions.

The term "bromostyrene" as used herein means para-bromo, meta-bromo, or ortho-bromo-styrene or a mixture of any of these. It will henceforth be termed "the product."

Bromostyrene is a well-known monomer, being either a para-meta-, or ortho-bromo derivative, or a mixture of these.

The advantage of the pyrolytic method over the catalytic method described in the British Patent No. 986,634 is that in the pyrolytic method the reaction tube used for pyrolysis can be easily cleaned from any tars formed during the reaction by simply burning them by passing air through the hot reactor.

A further improvement of the method involves the use of catalytic quantities of peroxides which, by forming free radicals, accelerate the reaction considerably and also eliminate any possible side reactions. Any suitable source of free radicals can be used, e.g. peroxides and hydroperoxides such as di-t-butyl peroxide, dicumyl peroxide, benzoyl peroxide, t-butyl hydroperoxide, hydrogen peroxide (dry or in water solution) or other decomposable species such as azobis-isobutyronitrile, lead tetraethyl or bromine. By using such compounds the temperature of the reaction can be decreased considerably, to a temperature as low as 280°C, and the result is a considerable reduction in power. Smaller reactors can be used as the reaction contact time is shorter.

Fuller details of the present invention are described in the following examples to which, however, it is not limited.

EXAMPLE 1

300 g $\beta$-bromoethyl-bromo-benzene were added through a motor driven syringe into the reactor at a rate of 60 g/h. Methanol was added at a rate of 14 g/h and nitrogen gas preheated to 300°C at a rate of 2 l/h. The reactor was a glass spiral made of a 6 mm wide 3 m long glass tube connected to a tube 30 mm wide and 25 cm long. The reactor was kept at a temperature of 490°–500°C. The liquid products were collected in a trap submerged in an ice bath while the methylbromide was trapped in a receptacle placed in liquid nitrogen. The liquid products were then subjected to fractional distillation in a vacuum to obtain 166 gr bromostyrene and 45 gr unconverted $\beta$-bromo-bromoethyl benzene. The yield is 94% based on reacted bromoethyl bromobenzene, 90% yield of methyl bromide was also obtained.

EXAMPLE 2

The experiment was carried out in the manner described in Example 1, but without methanol. The conversion was only 74% and the yield was only 44%. A substantial quantity of heavy products and tar-like materials were obtained.

EXAMPLE 3

170g $\beta$-bromoethyl dibromobenzene (being mainly a mixture of the ortho and para isomers) were driven into the reactor described in Example 1 at a rate of 20 gr/h together with methanol at a rate of 4.4gr/h and preheated nitrogen at a rate of 2 l/h. The products were distilled in vacuum and consisted of 14 gr unconverted product and 108 gr. dibromostyrene, namely 91% yield.

EXAMPLE 4

2 g di-t-butyl peroxide were dissolved in 100 g $\beta$-bromo ethyl bromo benzene. The mixture was added to the reactor in a manner described in Example 1, together with 25 g methanol and nitrogen at a flow rate of 2 l/h. The reactor was a glass spiral made of a 6 mm wide 5 m long tube heated to 300°–320°C. The products were collected as in Example 1 and consisted of 58 g bromostyrene and 12 g unconverted reactant. The yield was 95% bromostyrene.

EXAMPLE 5

170 g $\beta$-bromoethyl dibromobenzene containing 4 g di-t-butyl peroxide were injected into the reactor together with methanol as described in Example 3. The temperature of the reactor was 340°–360°C. The products after distillation consisted of 20 g unconverted reactant and 103 g dibromostyrene or 90% yield.

We claim:
1. A process for the production of bromostyrene and a lower alkyl bromide, which comprises reacting bromoethyl bromobenzene with a lower alkanol at a temperature in the range of 400°C. to 550°C.
2. A process as claimed in claim 1, wherein the lower alkanol is methanol and the lower alkyl bromide is methyl bromide.
3. A process as claimed in claim 1, wherein the lower alkanol is ethanol and the lower alkyl bromide is ethyl bromide.
4. A process as claimed in claim 1, wherein the starting material is $\alpha$-bromoethyl bromobenzene, $\beta$-bromoethyl bromobenzene or a mixture thereof.
5. A process as claimed in claim 1, wherein $\beta$-bromoethyl bromobenzene is reacted with methanol to form bromostyrene and methyl bromide.
6. A process as claimed in claim 1, wherein nitrogen is admixed with the reactants.

* * * * *

UNITED STATES PATENT OFFICE
CERTIFICATE OF CORRECTION

Patent No. 3,980,722     Dated  September 14, 1976

Inventor(s) ELLA COHEN et al

It is certified that error appears in the above-identified patent and that said Letters Patent are hereby corrected as shown below:

Column 1, line 10:  "p-bromoethyl" should read -- β-bromoethyl --.

Column 1, line 18:  "p-haloethyl" should read -- β-haloethyl --.

Signed and Sealed this

Ninth Day of November 1976

[SEAL]

Attest:

RUTH C. MASON
Attesting Officer

C. MARSHALL DANN
Commissioner of Patents and Trademarks